United States Patent [19]

Reverman

[11] 4,026,911
[45] May 31, 1977

[54] PROCESS FOR THE PREPARATION OF KETOALKYNOIC ACIDS AND USE OF THE PROCESS IN AN IMPROVED SYNTHESIS OF 2-(SUBSTITUTED)-CYCLO-PENTANE-1,3,4-TRIONES

[75] Inventor: Lawrence Francis Reverman, Elkhart, Ind.

[73] Assignee: Miles Laboratories, Inc., Elkhart, Ind.

[22] Filed: Feb. 23, 1976

[21] Appl. No.: 660,270

[52] U.S. Cl. .............................. 260/413; 260/340.9; 260/415; 260/468 D
[51] Int. Cl.$^2$ ..................... C11C 1/00; C07C 69/00
[58] Field of Search ............... 260/413, 415, 340.9, 260/468 D

[56] References Cited

UNITED STATES PATENTS

| 3,033,884 | 5/1962 | Osbond et al. | 260/413 |
|---|---|---|---|
| 3,824,262 | 7/1974 | Heslinga | 260/413 |

OTHER PUBLICATIONS

Heather; J. B. et al., "Total Synthesis of Prostaglandins V. A Synthesis of (−)-Prostaglandine$_2$ Via A Totally Asymmetric Process", Tetrahedron Letts. 25, pp. 2313–2316, (1973).

Sandler; S. R. et al., "Organic Functional Group Preparations", Academic Press, N.Y. (1968), pp. 68–69.

Morrison, R. T., et al., "Organic Chemistry", (third ed.), (1973), Allyn & Bacon, Boston, pp. 452 and 585–587.

Primary Examiner—Helen M. McCarthy
Attorney, Agent, or Firm—Myron B. Sokolowski

[57] ABSTRACT

Reaction of a 2-methyl-2-(alkenyl)-1,3-dioxolane with an $\alpha,\omega$-dihalogenoalkane to obtain a 2-methyl-2-($\omega$-chloroalkynyl)-dioxolane, conversion of the latter to a corresponding nitrile, and hydrolysis of the nitrile to form a ketoalkynoic acid is a novel process for preparing the acid.

Use of the process in the synthesis of 2-(substituted)-cyclopentane-1,3,4-triones improves that synthesis.

11 Claims, No Drawings

PROCESS FOR THE PREPARATION OF KETOALKYNOIC ACIDS AND USE OF THE PROCESS IN AN IMPROVED SYNTHESIS OF 2-(SUBSTITUTED)-CYCLO-PENTANE-1,3,4-TRIONES

BACKGROUND OF THE INVENTION

1. Field of the Invention

Ketoalkynoic acids and their esters that have the structural formula,

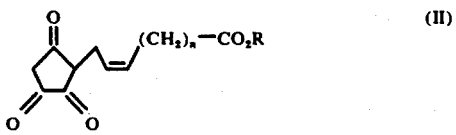
(I)

TABLE A

HEATHER SYNTHESIS OF 2-(6-CARBOMETHOXY-2-CIS-HEXENYL)-CYCLOPENTANE-1,3,4-TRIONE

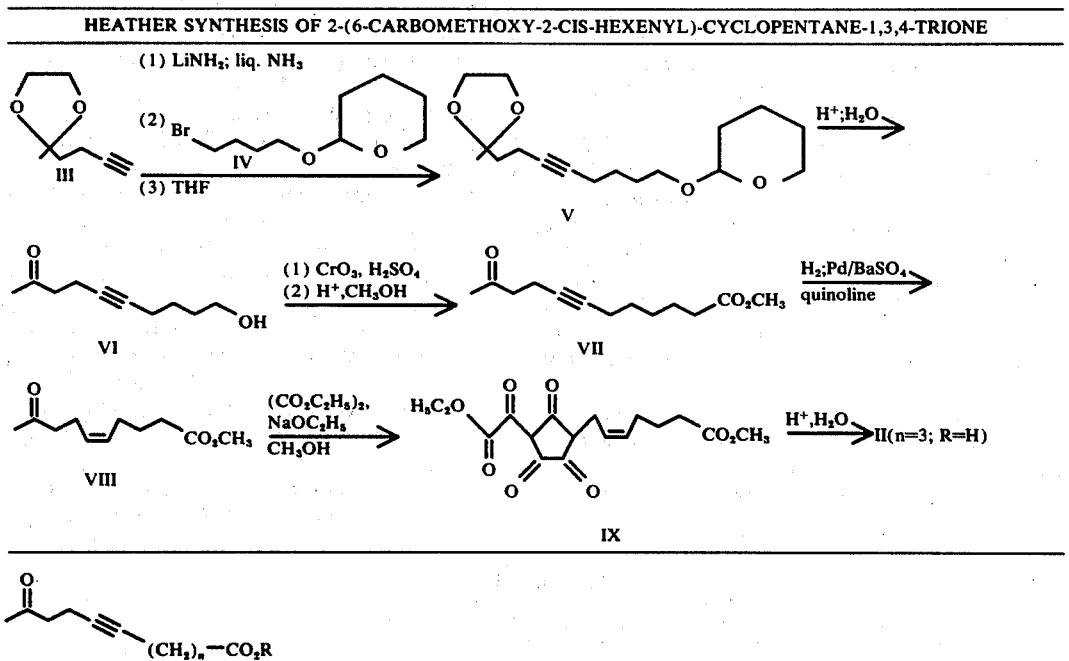

wherein and elsewhere in this specification $n$ is an integer of the set 1–8 and R is hydrogen atom or an alkyl group of 1–3 carbon atoms, are starting materials or intermediates in the synthesis of 2-(substituted)-cyclopentane 1,3,4-triones and their esters that have the general structure, (II)

Compounds II have anti-ulcerogenic properties (U.S. Pat. No. 3,558,682 [1971]) and utility as intermediates in the synthesis of prostaglandin $E_2$ and its analogues (Heather et al., *Tetrahedron Letters*, No. 25, 2315 [1973]; hereafter "Heather").

DESCRIPTION OF THE PRIOR ART

The Heather synthesis of 2-(6-carboxy-2-cis-hexynyl)-cyclopentane-1,3,4-trione implicitly includes a process for preparing 9-oxo-5-decynoic acid (I; $n=3$, R=H). Table A provides a synopsis of that synthesis which consists of: first treating 2-methyl-2-(3-butynyl)-1,3-dioxolane, III, with lithium amide in liquid ammonia and then with 1-bromo-4-tetrahydropyranyloxybutane, IV, in tetrahydrofuran to obtain 2-methyl-2-(8-pyranyloxy-3-oxtynyl)-1,3-dioxolane, V; hydrozyling V to 9-oxo-5-decyn-1-ol, VI; oxidizing VI with Jone's reagent (CrO$_3$, H$_2$SO$_4$) to 4-oxo-5-decynoic acid; esterifying the latter with methanol under acidic catalyss to obtain methyl-9-oxo-5-decynoate, VII; hydrogenating VII over Pd/BaSO$_4$ (lindlar's catalyst) in quinoline to get methyl 9-oxo-5-cis-decenoate, VIII; condensing VIII with diethyl oxlate in the presence of sodium ethoxide in ethanol to obtain 2-(6-carbomethoxy-2-cis-hexenyl)-5-(ethoxyalkyl)-cyclopentane-1,3,4-trione, IX; and hydrolyzing IX under acidic conditions to obtain 2-(6-carboxy-2-cis-hexenyl)-cyclopentane-1,3,4-trione (II:n=3: r=[H.

The preparation of 9-oxo-5-decynoate, VII, in the Heather pathway requires use of 1-bromo-4-tetrahydropyranyloxybutane, IV, to obtain VI and use of chromic oxidesulfuric acid to oxidize VI to the desired acid, VIII. Reagent IV is unstalb na commercially unavailable. Preparation of IV requires monotetrahydropyranylation of 1,4-butanediol, and treatment of the mesylate with lithium bromide in acetone, a preparation which is difficult to perform on a large scale. Use of chromic oxide-sulfuric acid to introduce the carboxyl group into VII has the attendant risk of further oxidation of the 9-keto group. The disclosed process obviates such difficulties.

SUMMARY OF THE INVENTION

The subject matter of this invention is: (A) a process for the preparation of ketoalkynoic acids and their esters having the formula,

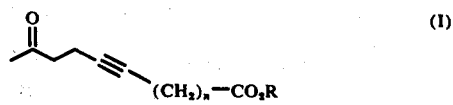
(I)

previously described; and (B) use of that process to improve the synthesis of 2-(substituted)-cyclopentane-1,3,4-triones of the formula,

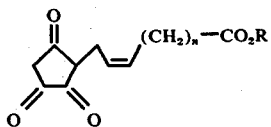

(II)

also previously described. In I and II, as well as elsewhere hereafter; n is an integer of the set 1–8; and R is a hydrogen atom or a methyl, ethyl, or propyl group.

Table B and the following commentary explain the steps comprising the process for preparation of compounds I:

A. Reaction of 2-methyl-2-(3-butynyl)-1,3-dioxolane, III, with a dihalogenoalkane, XI, in the presence of sodium, lithium, or potassium amide in liquid ammonia at from −50° C to 0° C (−30° C is preferred) for from 0.5 to 6 hours results in a 2-(methyl)-2-(ω-chloroalkynyl)-1,3-dioxolane, XII.

B. Conversion of XII to the nitrile, 2-(methyl)-2-(ω-cyanoalkynyl)-1,3-dioxolane (XIII), occurs in the presence of a cyanide salt in a polar organic solvent at reflux temperatures. Any cyanide salt can be utilized in this step, including but not limited to KCN, NaCN, LiCN, or $NH_4CN$. A convenient polar solvent is ethanol, but dimethylformamide, dimethylsulfoxide or other solvents can be used. Conversion occurs in about 4 to 48 hours depending on the cyanide salt and solvent utilized.

C. Hydrolysis of XIII to the ketoalkynoic acid, II, is effected by in the presence of strong base (NaOH, KOH) in the same solvents utilized in the preceding step at reflux temperatures. Completion of hydrolysis requires from 4 to 24 hours.

chloro-2-iodo-ethane; 1-chloro-3-bromo-propane; 1-chloro-3-iodopropane; 1-chloro-4-iodo-butane; 1-chloro-4-bromo-butane; 1-chloro-5-bromo-pentane; 1-chloro-5-iodo-pentane; 1-chloro-6-bromo-hexane; 1-chloro-6-iodo-hexane; 1-chloro-7-bromoheptane; 1-chloro-7-iodo-heptane; 1-chloro-8-bromo-octane; and 1-chloro-8-iodo-octane.

In a preferred embodiment of the process, 2-methyl-2-(3-butynyl)-1,3-dioxolane is reacted with 1-chloro-3-bromopropane or 1-chloro-3-iodo-propane, in the presence of lithium amide in liquid ammonia to obtain 2-methyl-2-(7-chloro-3-heptynyl)-1,3-dioxolane. Conversion of the latter to the nitrile, 2-methyl-2-(7-cyano-3-heptynyl)-1,3-dioxolane, is accomplished by reaction with sodium cyanide in ethanol under reflux. The nitrile is then hydrolyzed in sodium hydroxide to obtain the desired 9-oxo-5-decynoic acid.

This process eliminates the requirement of bromotetrahydropyranyloxyalkanes such as 1-bromo-4-tetrahydropyranyloxybutane. The process also provides for the facile introduction of the carboxylic group into the ketoalkynyl intermediate. In the Heather process carboxylation is accomplished by oxidation of 9-oxo-5-decyne-1-ol with chromic oxide and sulfuric acid. The present process requires simple displacement of a nitrile functional group with a carboxylic group under hydrolysis. Thus potential further oxidation of the keto group of the ketoalkynal intermediate is obviated.

This invention also is an improvement in the Heather process for the synthesis of 2-(carbalkoxyalkenyl)-cyclopentane-1,3,4-triones having formula II. Table C and the following explanation of that table provide a description of the improved process. Note that in Table C, symbols n, R, and R' have the same meanings as

TABLE B

PROCESS FOR THE SYNTHESIS OF KETOALKYNOIC ACIDS OR THEIR ESTERS

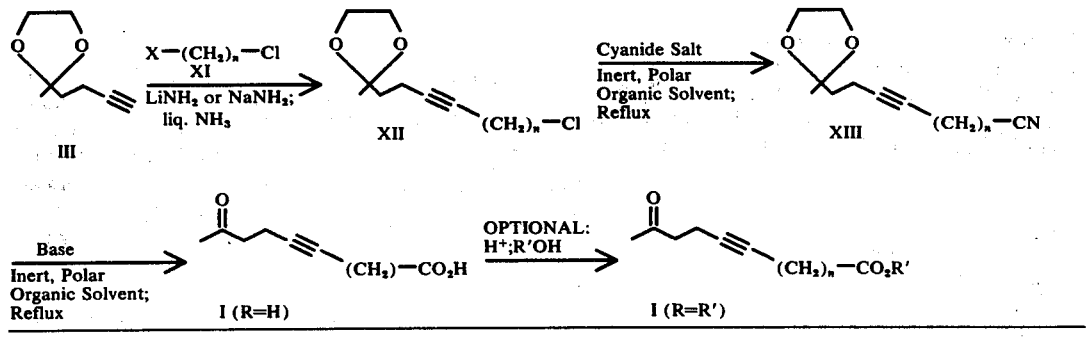

D. The ketoalkynoic acid optionally is esterified with a lower alkanol, R'OH in which R' is an alkyl group of 1–3 carbon atoms, under acid-catalyzed conditions.

The starting material, 2-methyl-2-(3-butynyl)-1,3-dioxolane is prepared according to the method described in Heather (*Tetrahedron Letters*, No. 25, 2313 at 2314 [1973]).

The dihalogenoalkanes, XI, are commercially available or are easily prepared according to standard methods known to organic chemistry (Morrison, R.T., and Boyd, R.N., *Organic Chemistry*, 2d Ed., Boston, Allyn and Bacon, pp. 464–465 and 529–530 [1966]). Among the dihalogenoalkanes represented by IV which are useful in this invention are: chlorobromomethane; chloroiodomethane; 1-chloro-2-bromo-ethane; 1- previously defined. The improved process utilizes 2-methyl-2-(3-butynyl)-1,3-dioxolane, II, as the starting material as reported in Heather. Conversion of II to a ketoalkynoic acid I (R=H) proceeds as described previously. Esterification of I with a lower alkanol, R'OH, under acidic conditions and under reflux, following by hydrogenation provides the corresponding alkyl keto-cis-alkenoate, VIIIa, treatment of which with a di(-loweralkyl)oxalate, $(CO_2R')_2$, an alkali-metal alkoxide, $(CO_2R')_2$ and a lower alkanol, R'OH, gives a 2-(carbalkoxy-cis-alkenyl)-5-alkoxyallyl-cyclopentane-1,3,4-trione intermediate, IXa. Treating IXa with acid provides the 2-(carbalkoxy)-cyclopentane-1,3,4-trione, II (R=R').

TABLE C
IMPROVED HEATHER SYNTHESIS

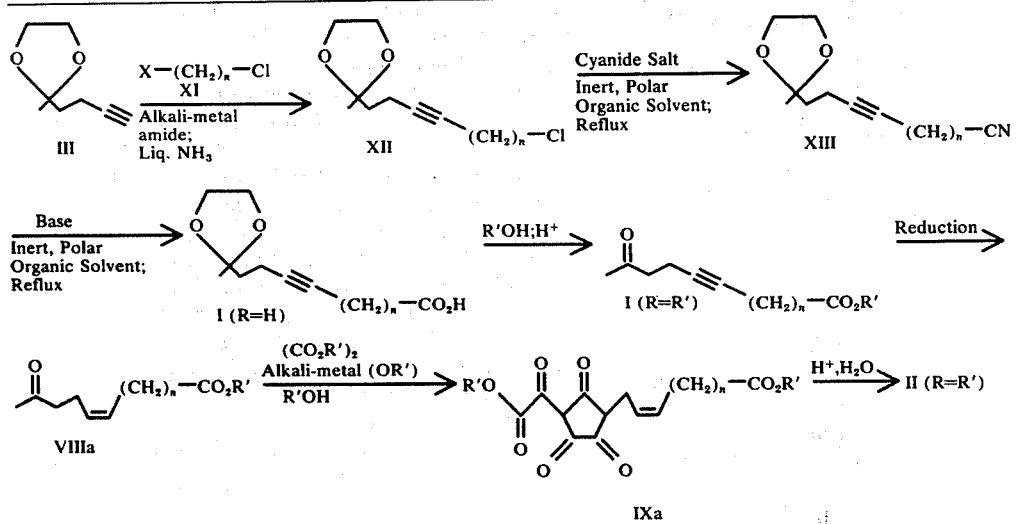

DESCRIPTION OF PREFERRED EMBODIMENTS

EXAMPLE 1

Method of Preparing Ketoalkynoic Acids

A. Reaction of 2-Methyl-2-(3-Butynyl)-1,3-Dioxolane and a Dihaloalkane (1-Chloro-3-Iodo-Propane) to Obtain a 2- Methyl-2-(Chloroalkynyl)-1,3-Dioxolane (1-Methyl-2-[7-Chloro-3-Heptynyl]-1,3-Dioxolane).

A solution of lithium amide (prepared from 3.5 g-atoms of lithium in 500 ml liquid NH₃) was stirred at −30° C while 2-methyl-2-(3-butynyl)-1,3-dioxolane (70.0 g, 0.5 mol) was added thereto dropwise over a 45 minute period. The solution was allowed to stir at −30° C for 1 hour and subsequently cooled to −60° C; 1-chloro-3-iodo-propane (103 g, 0.5 mol) then was added dropwise over a 30 minute period. After the addition was completed, the reaction was stirred at −30° C for 4 hours. Solid NH₄Cl (25 g, 0.47 mol) was added and the ammonia allowed to evaporate overnight. Water (200 ml) and ether (300 ml) were added to the solid residue and stirred for 15 minutes. The solution was filtered through infusorial earth (CELITE) and the layers separated. The aqueous layer was further extracted with ether (2 × 200 ml) and the combined organic layers washed with water, brine, and dried over anhydrous MgSO₄. Evaporation of the solvent gave 97 g of 2-methyl-2-(7-chloro-3-heptynyl)-1,3-dioxolane as an orange oil, bp 87°–88° C/ 0.15 mm. Yield: 65 g, 60%. NMR (CDCl₃): 1.28(s, 3H); 1.67–2.52(m, 8H); 3.62(s, 2H); and 3.9(s, 4H).

Substitution of chloro-iodo-methane, 1-chloro-2-iodoethane, 1-chloro-4-iodo-butane, 1-chloro-5-iodo-pentane, 1-chloro-6-iodo-hexane, 1-chloro-7-iodo-heptane, or 1-chloro-8-iodo-octane in lieu of the 1-chloro-3-iodo-propane respectively yields 2-methyl-2-(5-chloro-3-pentynyl), 2-methyl-2-(6-chloro-3-hexynyl)-, 2-methyl-2-(8-chloro-3-octynyl)-, 2-methyl-2-(9-chloro-3-nonynyl)-, 2-methyl-2 -(10-chloro-3-decynyl)-, 2-methyl-2-(11-chloro-3-undecynyl)-, or 2-methyl-2-(12-chloro-3-dodecynyl)-1,3-dioxolane. Use of chlorobromomethane, 1-chloro-2-bromoethane, 1-chloro-3-bromo-butane, 1-chloro-5-bromo-pentane, 1-chloro-6-bromo-hexane, 1-chloro-7-bromo-heptane, or 1-chloro-8-bromo-octane also provides the respective 2-methyl-2-(ω-chloroalkynyl)-1,3-dioxolane.

B. Converting the 2-Methyl-2-(Chloroalkynyl)-1,3-Dioxolane (2-Methyl-2-[7-Chloro-3-Heptynyl]-1,3-Dioxolane) to a Corresponding Nitrile (2-Methyl-2-[7-Cyano-3-Heptynyl]-1,3-Dioxolane.

2-Methyl-2-(7-chloro-3-heptynyl)-1,3-dioxolane (21.6 g, 0.1 mol) was dissolved in 120 ml EtOH (convenience; dimethylformamide, dimethylsulfoxide, or other polar solvents may be used) and added to a solution of NaCN (9.8 g, 0.2 mol) and NaI (2.0 g, 0.013 mol) in 80 ml H₂O. KCN, NH₄CN or other cyanide salts may be used. The reaction was concentrated to remove the solvent and was extracted with three 100 ml portions of ether. The combined organic extracts were washed with 2–50 ml portions of water and brine. After drying over anhydrous MgSO₄, the solvent was removed to give 20 g of 2-methyl-2-(7-cyano-3-heptynyl)-1,3-dioxolane, pure enough to use directly in the next step. Yield: 20 g, 99%. IR (CHCl₃): 3000, 2950, 2890, 2250, 1675 cm⁻¹.

If 2-(methyl)-2-(5-chloro-3-pentynyl)-, 2-(methyl)-2-(6-chloro-3-hexynyl)-, 2-(methyl)-2-(8-chloro-3-octynyl)-, 2-(methyl)-2-(9-chloro-3-nonynyl)-, 2-methyl)-2-(10-chloro-3-decynyl)-, 2-(methyl)-2-(11-chloro-undecynyl)-, or 2-(methyl)-2-(12-chloro-3-dodecynyl)-1,3-dioxolane is substituted in the above step for 2-methyl-2-(7-chloro-3-heptynyl)-1,3-dioxolane, the above procedure respectively provides 2-methyl-2-(5-cyano-3-pentyl)-, 2-methyl-2-(6-cyano-3-hexynyl)-, 2-methyl-2-(8-cyano-3-octynyl)-, 2-methyl-2-(9-cyano-3-nonynyl)-, 2-methyl-2-(10-cyano-3-decynyl)-, 2-methyl-2-(11-cyano-3-undecenyl)-, or 2-methyl-2-(12-cyano-3-dodecenyl)-1,3-dioxolane.

C. Hydrolysis of the 2-Methyl-2-(Cyanoalkynyl)-1,3-Dioxolane (2-Methyl-2-[7-Cyano-3-Heptynyl]-1,3-Dioxolane) to a Ketoalkynoic Acid (9-Oxo-5-Decynoic Acid)

The 2-(methyl)-2-(7-cyano-3-heptynyl)-1,3-dioxolane (20 g, 0.1 mol) was dissolved in 200 ml EtOH and 200 ml 10N NaOH. The reaction was stirred at reflux until no more NH₃ was evolved (20 hours). The cooled reaction was then poured into 500 ml H₂O and extracted with 3—200 ml portions of ether. The aqueous phase was acidified with concentrated HCl and allowed to stir 2 hours at room temperature. The acid solution was extracted with ethyl acetate and the combined organic extracts were washed with H₂O, brine, and dried over anhydrous MgSO₄. Evaporation of the solvent gave 15.5 g (85%) of 9-oxo-5-decynoic acid as a red oil. NMR (CDCl₃): 1.6–2.8(m, 11HO; 2.17(s, 3H); and 10.4(s, 1H). IR (CHCl₃): 2400–3400, 1710 cm⁻¹.

When 2-methyl-2-(5-cyano-3-pentynyl)-, 2-methyl-2-(6-cyano-3-hexynyl)-, 2-methyl-2-(8-cyano-3-octynyl)-, 2-methyl-2-(9-cyano-3-jonynyl)-, 2-methyl-2-(10-cyano-3-decynyl)-, 2-methyl-2-(11-cyano-3-undecynyl)-, or 2-methyl-2-(12-cyano-3-dodecynyl)-1,3-dioxolane is substituted for 2-methyl-2-(7-cyano-3-heptynyl)-1,3-dioxolane in this step, the above procedure respectively yields: 7-oxo-3-octynoic, 8-oxo-4-nonynoic, 10-oxo-6-undecynoic, 11-oxo-7-dodecynoic, 12-oxo-8-tridecynoic, 13-oxo-9-tetradecynoic, or 14-oxo-10-pentadecynoic acid.

EXAMPLE 2

Preparation of 2-(6-Carbomethoxy-Cis-2-Hexenyl)-Cyclopentane-1,3,4-Trione

Crude 9-oxo-5-decynoic acid (15.5 g, 0.085 mol) obtained by the process described in Example 1, was dissolved in 150 ml MeOH and treated with 15 drops concentrated HCl. After standing overnight at room temperature (convenience), the solvent was evaporated. The residue was dissolved in ether, and washed with H₂O, saturated aqueous NaHCO₃ solution, water, brine, and dried over anhydrous MgSO₄. Evaporation of the solvent gave 14.3 g (87%) of crude methyl 9-oxo-5-decynoate as a yellow oil. NMR (CDCl₃): 1.57–3.00(m, 13HO, 2.17(s, 3H), 3.67(s, 3H).

The methyl 9-oxo-5-decynoate (31.5 g, 0.16 mol) was dissolved in 250 ml MeOH containing 0.6 quinoline. Five percent of Pd/BaSO₄ (0.6 g) was added. One equivalent of H₂ was absorbed at room temperature and 1 atm in 35 minutes. The catalyst was filtered, the solvent evaporated, and the residue taken up in 500 ml of ethyl acetate. It was washed twice with 125 ml 1N HCl, H₂O, and brine. After drying over anhydrous MgSO₄, the solvent was removed and distillation gave 24 L g (80%) of methyl 9-oxo-cis-decenoate as a colorless oil, bp 93–94° C/0.4 mm. The NMR spectrum was identical to an authentic sample prepared by the Sih process. NMR (CDCl₃): 1.3–2.6(m, 10H), 2.13(s, 3H), 3.65(s, 3H), 5.2–5.5ppm(m, 2H).

Diethyl oxalate (7.5 g, 0.055 mol) and methyl 9-oxo-5-cis-decenoate (5.0 g, 0.025 mol) were added dropwise to a solution of NaOEt (prepared from 1.4 g-atoms of Na and 25 ml EtOH) at 0.5° C over 30 minutes. Reaction was then allowed to warm to room temperature, stirred for 2 hours, then heated to 70° C for 1 hour. Mixture was cooled to 10° C and 4 ml acetic acid added. Solvent was then evaporated off at 40° C on a rotary evaporator, and a brown residue was taken up in 200 ml 2N HCl and refluxed for 4 hours. Upon cooling, the acid solution was decanted from a brown oily residue and extracted with ethyl acetate (3 × 200 ml). The combined organic extracts were washed with H₂O, brine, and dried over anhydrous MgSO₄. (TLC showed that the product was identical to that of an authentic sample). The solvent was stripped to give 8 g of a red oil. That oil was taken up in 100 ml EtOH and treated with 0.5 ml concentrated HCl and allowed to stand at room temperature overnight (convenience) Solvent was stripped; the residue was taken up in 300 ml ethyl acetate, washed twice with 50 ml H₂O, brine, and dried over anhydrous MgSO₄. Evaporation of solvent gave 7.5 g of a dark red oil which was chromatographed on 150 g Silica Gel with benzene/ethyl acetate, (7/3) to give 3 g (40%) of an orange oil. IR and NMR spectra were identical to an authenic sample.

What is claimed is:

1. A process for preparing a ketoalkynoic acid or its ester having the structure,

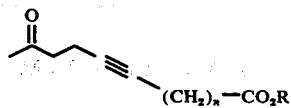

wherein and elsewhere hereafter n is an integer of the set 1–8 and R is selected from the group consisting of a hydrogen atom or a loweralkyl radical having from 1 to 3 carbon atoms, comprising:
   a. reacting 2-methyl-2-(3-butynyl)-1,3-dioxolane with a α,ω-dihalogenoalkane selected from the group consisting of Br-(CH₂)ₙ-Cl or I-(CH₂)ₙ-Cl in liquid ammonia in the presence of an alkali-metal amide to obtain a 2-methyl-2-(ω-chloroalkynyl)-1,3-dioxolane of the formula,

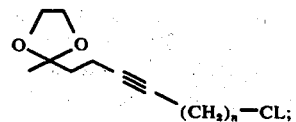

b. converting the 2-methyl-2-(ω-chloroalkynyl)-1,3-dioxolane to a corresponding nitrile having the structure,

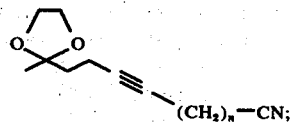

with a cyanide salt in a polar organic solvent;
   c. hydrolyzing the nitrile under alkaline conditions to obtain the corresponding ketoalkynoic acid;
   d. and optionally esterifying the ketoalkynoic acid with an alcohol selected from the group consisting of methanol, ethanol, or propanol.

2. The process in claim 1 wherein the α,ω-dihalogenoalkane in step (a) is selected from the group consisting of: chlorobromomethane, chloroiodomethane, 1-chloro-2-bromo-ethane, 1-chloro-2-iodoethane, 1-chloro-3-bromopropane, 1-chloro-3-iodopropane, 1-chloro-4-bromobutane, 1-chloro-4-iodobutane, 1-chloro-5-bromopentane, 1-chloro-5-iodopentane, 1-chloro-6-bromohexane, 1-chloro-6-iodohexane, 1-chloro-7-bromoheptane, 1-chloro-7-iodoheptane, 1-chloro-8-bromooctane, and 1-chloro-8-iodooctane.

3. The process in claim 1 wherein the 2-methyl-2-(ω-chloroalkynyl)-1,3-dioxolane in step (a) is selected from the group consisting of: 2-methyl-2-(5-chloro-3-pentynyl)-1,3-dioxolane, 2-methyl-2-methyl-2-(6-chloro-3-hexynyl)-1,3-dioxolane, 2-methyl-2-(7-chloro-3-heptynyl)-1,3-dioxolane, 2-methyl-2-(8-chloro-3-octynyl)-1,3-dioxolane, 2-methyl-2-(9-chloro-3-nonynyl)-1,3-dioxolane, 2-methyl-2-(10-chloro-3-decynyl)-1,3-dioxolane, 2-methyl-2-(11-chloro-3-undecynyl)-1,3-dioxolane, and 2-methyl-2-(12-chloro-3-dodecynyl)-1,3-dioxolane.

4. The process in claim 1 wherein the alkali-metal amide is selected from the group consisting of sodium amide, potassium amide, or lithium amide.

5. The process in claim 1 wherein the nitrile obtained in step (b) is selected from the group consisting of: 2-methyl-2-(5-cyano-3-pentynyl)-1,3-dioxolane, 2-methyl-2-(6-cyano-3-hexynyl)-1,3-dioxolane, 2-methyl-2-(7-cyano-3-heptynyl)-1,3-dioxolane, 2-methyl-2-(8-cyano-3-octynyl)-1,3-dioxolane, 2-methyl-2-(9-cyano-3-nonynyl)-1,3-dioxolane, 2-methyl-2-(10-cyano-3-decynyl)-1,3-dioxolane, 2-methyl-2-(11-cyano-3-undecynyl)-1,3-dioxolane, and 2-methyl-2-(12-cyano-3-dodecynyl)-1,3-dioxolane.

6. The process in claim 1 wherein the cyanide salt utilized in step (b) is selected from the group consisting of sodium cyanide, potassium cyanide, lithium cyanide, ammonium cyanide, or cuprous cyanide.

7. The process in claim 1 wherein the polar organic solvent used in step (b) is selected from the group consisting of: ethanol, acetone, dimethylformamide, acetonitrile, nitromethane, or dimethylsulfoxide.

8. The process in claim 1 wherein the ketoalkynoic acid obtained in step (c) is selected from the group consisting of: 7-oxo-3-octynoic acid, 8-oxo-3-nonynoic acid, 9-oxo-3-decynoic acid, 10-oxo-3-undecynoic acid, 11-oxo-3-dodecynoic acid, 12-oxo-3-tridecynoic acid, 13-oxo-3-tetracynoic acid, and 14-oxo-3-pentadecynoic acid.

9. A process for preparing 9-oxo-5-decynoic acid comprising:
a. reacting 2-methyl-2-(3-butynyl)-1,3-dioxolane with a α,ω-dihalogenoalkane selected from the group consisting of 1-chloro-3-bromopropane or 1-chloro-3-iodopropane in liquid ammonia in the presence of lithium amide to obtain 2-methyl-2-(7-chloro-3-heptynyl)-1,3-dioxolane;
b. converting the 2-methyl-2-(7-chloro-3-heptynyl)-1,3-dioxolane to 2-methyl-2-(7-cyano-3-heptynyl)-1,3-dioxolane with sodium cyanide in ethanol under reflux;
and hydrolyzing the 2-methyl-2-(7-cyano-3-heptynyl)-1,3-dioxolane to 9-oxo-5-decynoic acid under alkaline conditions.

10. In a process for the synthesis of a 2-(substituted)-cyclopentane-1,3,4-trione having the formula,

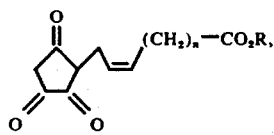

in which as well as elsewhere hereafter n is an integer having a value of from 1 to 8 and R is an alkyl group of 1–3 carbon atoms, by stepwise converting 2-methyl-2-(3-butynyl)-1,3-dioxolane to a ketoalkynoic acid of the formula

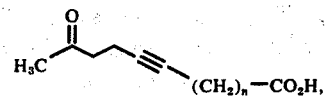

reducing teh ketoalkynoic acid to a corresponding keto-cis-alkenoic acid of the formula

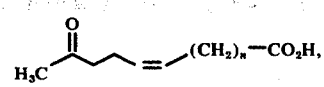

esterifying the cis-ketoalkenoic acid with a lower alkanol, R'OH in which and elsewhere hereafter R' is an alkyl group of 1–3 carbon atoms, under acidic conditions to a correspnding alkyl keto-cis-alkenoate of the formula,

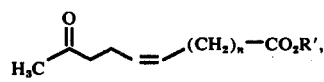

condensing the alkyl keto-cis-alkenoate with a di(-loweralkyl)oxalate of the formula, $(CO_2R')_2$, with a lower alkoxide, $(—OR')$, in the presence of an alkali-metal to obtain a 2-(substituted)-5-alkoxyalyl-cyclopentane-1,3,4-trione intermediate of the formula,

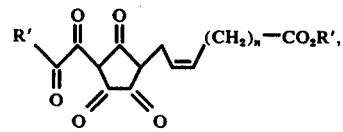

and hydrolyzing the intermediate to obtain the corresponding 2-substituted-cyclopentane-1,3,4-trione, the improvement which comprises:
a. reacting 2-methyl-2-(3-butynyl)-1,3-dioxolane with a α,ω-dihalogenoalkane selected from the group consisting of $Br—(CH_2)_n—Cl$ or $I—(CH_2)_n—Cl$ in liquid ammonia in the presence of an alkali-metal amide to obtain a 2-methyl-2-(ω-chloroalkynyl)-1,3-dioxolane of the formula,

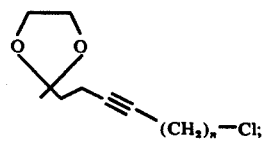

b. converting the 2-methyl-2-(ω-chloroalkynyl)-1,3-dioxolane to a corresponding nitrile having the structure,

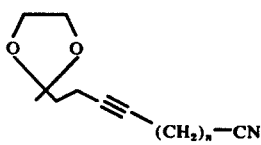

with a cyanide salt in a polar organic solvent; and c. hydrolyzing the nitrile under alkaline conditions to obtain the corresponding ketoalkynoic acid;

11. In a process for the synthesis of 2-(6-carbomethoxy-cis-hexenyl)-cyclopentane-1,3,4-trione by stepwise converting 2-methyl-2-(3-butynyl)-1,3-dioxolane to 9-oxo-5-decynoic acid, esterifying that acid to methyl 9-oxo-5-decynoate, reducing the latter to 9-oxo-cis-5-decenoate, condensing the methyl 9-oxo-cis-5-decenoate with diethyl oxalate to obtain 2-(6-carbomethoxy-cis-2-hexenyl)-5-ethoxalyl-cyclopentane-1,3,4-trione as an intermediate, and hydrolyzing the intermediate to obtain 2-(6-carbomethoxy-cis-hexenyl)-cyclopentane-1,3,4-trione, the improvement which comprises:

a. reacting 2-methyl-2-(3-butynyl)-1,3-dioxolane with 1-chloro-3-lowerpropane in the presence of lithium amide in liquid ammonia to obtain 2-methyl-2-(7-chloro-3-heptynyl)-1,3-dioxolane;

b. converting 2-methyl-2-(7-chloro-3-heptynyl)-1,3-dioxolane to 2-methyl-2-(7-cyano-3-heptynyl)-1,3-dioxolane with sodium cyanide in ethanol under reflux; and c. hydrolyzing the 2-methyl-2-(7-cyano-3-heptynyl)-1,3-dioxolane under alkaline conditions to obtain 9-oxo-5-decynoic acid.

* * * * *

UNITED STATES PATENT AND TRADEMARK OFFICE
CERTIFICATE OF CORRECTION

PATENT NO. : 4,026,911
DATED : May 31, 1977
INVENTOR(S) : Lawrence Francis Reverman It is certified that error appears in the above-identified patent and that said Letters Patent are hereby corrected as shown below:

Column 2, Line 1, change "hydrozyling" to --hydrolyzing--.
Column 2, Line 3, change "4" to --9--.
Column 2, Line 4, change "catalyss" to --catalysis--.
Column 2, Line 13, change ": n=[H" to --; R=H)--.
Column 2, Line 46, change "unstab na" to --unstable and--.
Column 2, Line 48, after "butanediol", insert --mesylation,--.
Column 3, Line 17, after "to", insert --O--.
Column 5, Line 48, after "ITE", insert --®--.
Column 7, Line 22, change "(9-cyano-3-jonynyl)" to --(9-cyano-3-nonynyl)--.
Column 7, Line 56, after "24", delete "L".
Column 10, Line 11, change "teh" to --the--.
Column 10, Line 32, change "alkoxyalyl" to --alkoxyalkyl--.

Signed and Sealed this

Thirteenth Day of June 1978

[SEAL]

Attest:

RUTH C. MASON
Attesting Officer

DONALD W. BANNER
Commissioner of Patents and Trademarks